(12) United States Patent
Cinader, Jr. et al.

(10) Patent No.: US 9,532,854 B2
(45) Date of Patent: *Jan. 3, 2017

(54) LINGUAL ORTHODONTIC APPLIANCE WITH REMOVABLE SECTION

(71) Applicant: 3M INNOVATIVE PROPERTIES COMPANY, St. Paul, MN (US)

(72) Inventors: David K. Cinader, Jr., Walnut, CA (US); Philip P. Soo, Woodbury, MN (US); James D. Cleary, Glendora, CA (US); Oliver L. Puttler, La Crescenta, CA (US)

(73) Assignee: 3M Innovative Properties Company, St. Paul, MN (US)

(*) Notice: Subject to any disclaimer, the term of this patent is extended or adjusted under 35 U.S.C. 154(b) by 160 days.

This patent is subject to a terminal disclaimer.

(21) Appl. No.: 14/461,083

(22) Filed: Aug. 15, 2014

(65) Prior Publication Data

US 2014/0356799 A1 Dec. 4, 2014

Related U.S. Application Data

(63) Continuation of application No. 12/936,399, filed as application No. PCT/US2009/038157 on Mar. 25, 2009, now Pat. No. 8,827,697.

(Continued)

(51) Int. Cl.
*A61C 3/00* (2006.01)
*A61C 7/30* (2006.01)
(Continued)

(52) U.S. Cl.
CPC . *A61C 7/30* (2013.01); *A61C 7/10* (2013.01); *A61C 7/145* (2013.01); *A61C 7/006* (2013.01); *Y10T 29/49568* (2015.01)

(58) Field of Classification Search
CPC ............ A61C 7/08; A61C 7/145; A61C 7/566
(Continued)

(56) References Cited

U.S. PATENT DOCUMENTS 2,266,860 A 12/1941 Griesinger
3,464,114 A * 9/1969 Brader ................. A61C 7/12
433/10

(Continued)

FOREIGN PATENT DOCUMENTS

BE 1005594 11/1993
DE 2733472 2/1978
(Continued)

OTHER PUBLICATIONS

International Search Report PCT/US2009/038157 5 pages; Oct. 18, 2010.

*Primary Examiner* — Nicholas Lucchesi
*Assistant Examiner* — Matthew Saunders (57) ABSTRACT

An aesthetic, partially removable orthodontic appliance is described, including a polymeric body that conforms to the lingual soft tissue and at least one wire member extending from the polymeric body. Each wire member releasably engages with a respective anchor that is, in turn, connected to the lingual surface of a respective tooth when the polymeric body is moved in a generally gingival direction into abutting relationship with the lingual soft tissue. Other features of the appliance include self-guiding magnetic couplings and couplings based on interlocking mechanical structures that provide releasable engagement between the removable section and the anchors, as well as related methods for making and using the same.

21 Claims, 3 Drawing Sheets

Related U.S. Application Data (60) Provisional application No. 61/043,495, filed on Apr. 9, 2008.

(51) Int. Cl.
*A61C 7/10* (2006.01)
*A61C 7/14* (2006.01)
*A61C 7/00* (2006.01)

(58) Field of Classification Search
USPC .......................................... 433/6–19
See application file for complete search history.

(56) References Cited

U.S. PATENT DOCUMENTS

| | | | |
|---|---|---|---|
| 4,054,996 A | 10/1977 | Wallshein | |
| 4,292,025 A * | 9/1981 | Forster | A61C 7/00 433/18 |
| 4,571,178 A * | 2/1986 | Rosenberg | A61C 7/10 433/18 |
| 5,064,370 A * | 11/1991 | Jones | A61C 7/00 433/18 |
| 5,310,340 A * | 5/1994 | Zedda | A61C 7/00 433/18 |
| 5,785,520 A * | 7/1998 | Carano | A61C 7/00 433/18 |
| 6,227,851 B1 | 5/2001 | Chishti | |
| 6,302,688 B1 | 10/2001 | Jordan | |
| 6,394,801 B2 | 5/2002 | Chishti | |
| 6,582,226 B2 | 6/2003 | Jordan | |
| 6,604,943 B2 * | 8/2003 | White | A61C 7/00 433/21 |
| 6,716,030 B1 | 4/2004 | Bulard | |
| 6,726,475 B2 | 4/2004 | Lin | |
| 6,739,870 B2 | 5/2004 | Lai | |
| 6,776,614 B2 | 8/2004 | Wiechmann | |
| 7,014,460 B2 | 3/2006 | Lai | |
| 7,020,963 B2 | 4/2006 | Cleary | |
| 7,234,934 B2 * | 6/2007 | Rosenberg | A61C 7/12 433/6 |
| 7,252,505 B2 | 8/2007 | Lai | |
| 8,827,697 B2 * | 9/2014 | Cinader, Jr. | 433/6 |
| 2003/0044746 A1 * | 3/2003 | Marotta | A61C 7/14 433/18 |
| 2003/0091952 A1 | 5/2003 | Bowman | |
| 2005/0003321 A1 | 1/2005 | Wiechmann | |
| 2005/0084815 A1 | 4/2005 | Paulus | |
| 2005/0158686 A1 | 7/2005 | Wiechmann | |
| 2005/0170309 A1 | 8/2005 | Raby | |
| 2005/0277084 A1 | 12/2005 | Cinader, Jr. | |
| 2006/0073435 A1 | 4/2006 | Stark | |
| 2006/0073436 A1 | 4/2006 | Raby | |
| 2006/0105286 A1 | 5/2006 | Raby | |
| 2006/0166160 A1 | 7/2006 | Cleary | |
| 2006/0177791 A1 | 8/2006 | Cinader, Jr. | |
| 2007/0031774 A1 | 2/2007 | Cinader, Jr. | |
| 2007/0092849 A1 | 4/2007 | Cosse | |
| 2007/0264607 A1 | 11/2007 | Olavarria | |
| 2008/0233531 A1 | 9/2008 | Raby | |
| 2010/0219546 A1 | 9/2010 | Puttler | |

FOREIGN PATENT DOCUMENTS

| | | |
|---|---|---|
| EP | 0334256 | 9/1989 |
| EP | 0551800 | 7/1993 |
| WO | WO 2007/128969 | 11/2007 |

* cited by examiner

LINGUAL ORTHODONTIC APPLIANCE WITH REMOVABLE SECTION

CROSS REFERENCE TO RELATED APPLICATIONS

This application is a divisional application of U.S. Utility application Ser. No. 12/936,399, filed on Mar. 25, 2009, which is a national stage filing under 35 U.S.C. 371 of PCT/US2009/038157, filed Mar. 25, 2009, which claims priority to Provisional Application No. 61/043,495, filed Apr. 9, 2008, the disclosure of which is incorporated by reference in its/their entirety herein.

BACKGROUND OF THE INVENTION

1. Field of the Invention

This invention broadly pertains to an appliance used in orthodontic treatment. More particularly, it pertains to an aesthetic orthodontic appliance that is at least partially removable.

2. Description of the Related Art

Orthodontics is the area and specialty of dentistry associated with the supervision, guidance, and correction malpositioned teeth into proper locations. Orthodontic treatment can be useful in correcting defects in a patient's bite (also called occlusion) along with promoting better hygiene and improving the overall aesthetics and health of the teeth.

Orthodontic treatment often involves the use of tiny slotted appliances known as brackets, which are generally affixed to the patient's anterior, cuspid, and bicuspid teeth. After the brackets have been placed on the teeth, an archwire is received into the slot of each bracket and acts as a track to guide the movement of respective teeth to orthodontically correct positions. End sections of the archwire are typically captured in appliances known as buccal tubes that are affixed to the patient's molar teeth. The brackets, archwires, and buccal tubes are typically referred to collectively as "braces".

However, conventional braces have inherent limitations. For example, brackets and wires in the mouth tend to trap food and plaque, especially in areas behind the archwire and beneath bracket tiewings. The poor oral hygiene that results from plaque build up, in turn, can lead to a host of other problems, including tooth decay, gingivitis, periodontal disease, amongst others. Plaque build up in the vicinity of the brackets in particular can also cause decalcification and so-called "white spot" lesions on enamel surfaces that remain even after the braces are removed at the end of treatment.

Removable appliances can significantly alleviate some of these problems by providing an ability to remove the orthodontic appliance from the mouth while eating and/or brushing. Not only do removable appliances facilitate the maintenance and cleaning of the teeth, they also facilitate cleaning of the appliance. Popular removable appliances include polymeric aligner shells manufactured by Align Technology (Santa Clara, Calif.), which are intended to incrementally and progressively re-position teeth to a desired teeth arrangement. Other types of appliances include wire-embedded appliances such as those based on the Hawley retainer or Crozat appliance, which typically use metal wires that passively contact the teeth surfaces. While these appliances can be used to effect corrective tooth movements, they are most commonly used for retention of teeth after correction has been completed. Spring aligners, also called spring retainers, combine aspects of both clear aligners and wire-embedded retainers and can be used for orthodontic correction. However, these too are limited in the types of forces they can apply on teeth, which in turn impact the breadth of dental malocclusions that can be treated.

SUMMARY OF THE INVENTION

Current removable appliances, while offering certain hygiene benefits, also have shortcomings related to treatment efficacy. Polymeric shells, for example, tend to be limited in their ability to correct particular dental malocclusions. Extrusion, gap closure, and molar teeth movement can be difficult or impossible to achieve, since these appliances rely on relatively weak mechanical retention between the shell and the teeth. Moreover, polymeric aligners are not entirely aesthetic even when clear, since they still cover the facial teeth surfaces and can stain or trap dark liquids such as coffee. On the other hand, retainer-like appliances that use springs or clasps that engage with teeth suffer from many of the same shortcomings as polymeric aligners. These appliances, as a whole, do not positively engage with the teeth in a manner that allows precise torque, angulation, rotational, and translational control. Further, many of these devices are generally not aesthetic since they use a facial wire residing over the facial surface of the teeth to prevent proclination of the teeth. Even more significantly, none of the above appliances are capable of controlling the forces directed to each individual tooth using anchorage from a portion of the dental structure, such as the palate, that does not change during treatment.

The present invention is directed to an aesthetic, lingual orthodontic appliance along with methods of making and using the same. This orthodontic appliance provides a level of control over forces applied to teeth comparable to that of fixed appliances. However, this appliance is at least partially removable, thereby providing the advantages of improved oral hygiene offered by removable appliances. As a further advantage, this appliance provides for a controlled and secure connection between the appliance and the teeth, while allowing easy disconnection therefrom.

In one aspect, the invention is directed to an orthodontic appliance including a removable section including a polymeric body and at least one wire member extending outwardly from the body, where each wire member includes an outer end portion and where the body includes an outer surface with a configuration that generally matches the configuration of a patient's lingual soft tissue, and at least one anchor, each anchor having a base for connecting the anchor to the lingual surface of a tooth, where the outer end portion of each wire member is releasably connected to a respective anchor when each anchor is connected to a respective tooth of a dental patient and the removable section is moved in a generally gingival direction into abutting relationship with the patient's lingual soft tissue.

In another aspect, the invention is directed to a method of making an orthodontic appliance, including connecting at least one anchor to one or more respective teeth on a physical dental model, forming a polymeric body against the physical dental model such that the outer surface of the polymeric body generally matches the configuration of the lingual soft tissue of the physical dental model, attaching at least one wire member to the polymeric body to form a removable section, where each wire member includes an outer end portion, and configuring each wire member such that the outer end portion of the wire member releasably connects with a respective anchor when the removable section is moved in a generally gingival direction into abutting relationship with the replica lingual soft tissue.

In another aspect, the present invention is directed to a method of verifying an orthodontic appliance on a physical dental model, including providing a dental appliance with at least one anchor and a removable section, where the removable section includes a polymeric body and at least one wire member extending outwardly from the body, where each wire member includes an outer end portion, and where the body includes an outer surface with a configuration that generally matches the configuration of a patient's lingual soft tissue, connecting each anchor to a respective tooth on the physical dental model, seating the removable section against the physical dental model, and observing that the outer ends of each wire member releasably connect to a respective anchor as the removable section is seated against the physical dental model.

In still another aspect, the present invention is directed to a method of orthodontic treatment including attaching at least one anchor to a lingual surface of a respective tooth, providing a removable section including a polymeric body and at least one wire member extending outwardly from the body, where each wire member includes an outer end portion, and releasably connecting the outer end portion of each wire member to a respective anchor as the removable section is moved in a generally gingival direction.

DEFINITIONS

As used herein:

"Mesial" means in a direction toward the center of the patient's curved dental arch.

"Distal" means in a direction away from the center of the patient's curved dental arch. "Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

Figure 1:
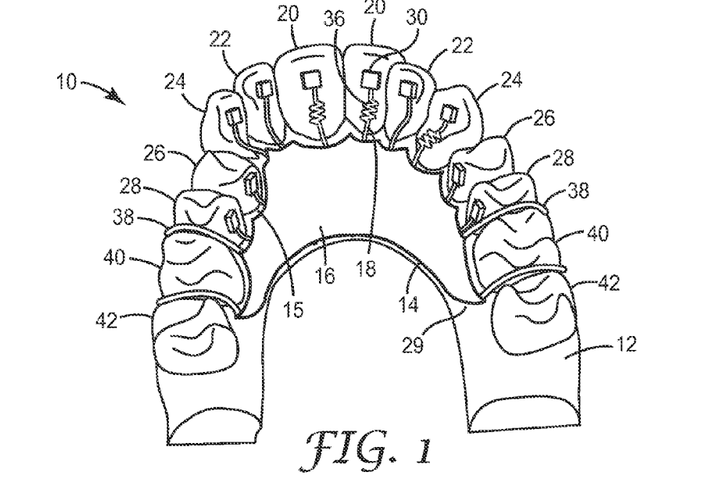
FIG. 1 is a perspective view of an upper arch appliance according to one embodiment of the present invention attached to a physical dental model.
Figure 2:
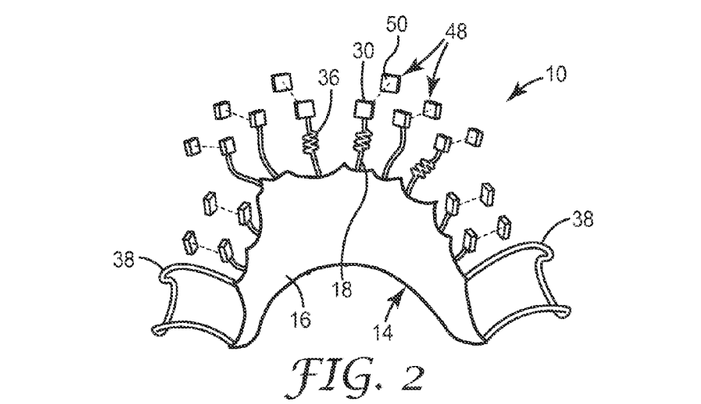
FIG. 2 is an exploded, perspective view of the appliance of FIG. 1 detached from the physical dental model.

The present invention is directed to lingual appliances that are customized to the patient, at least partially removable, and may be used to retain, or alternatively change the position of, one or more teeth of the upper or lower dental arch. An exemplary appliance in accordance with one embodiment of the invention is shown for the upper dental arch in FIGS. 1 and 2, and is broadly designated by the numeral 10. Upper arch appliance 10 includes a removable section 14 along with a plurality of corresponding anchors 48 (not visible in FIG. 1) that are, in turn, connected to the lingual tooth surfaces of a physical dental model 12. Dental model 12, which may be constructed of orthodontic stone (plaster of Paris) or epoxy resin, is a positive replica of a patient's upper central 20, lateral 22, cuspid 24, first bicuspid 26, second bicuspid 28, first molar 40, and second molar 42 teeth, as well as gingiva and lingual soft tissues collectively designated 29. Depending on the patient, it is possible that one or more of the teeth 20,22,24,26,28 may be absent at the outset of treatment. FIG. 2 also shows the removable section 14 and anchors 48, except in exploded view and with the dental model 12 removed for clarity. While the following detailed description of the appliance 10 references the dental model 12 by way of illustration and example, it is to be understood that the same description may similarly apply to intraoral application of the appliance 10. In the description below, for example, the appliance 10 may just as appropriately be described with reference to the dental structure of a patient undergoing orthodontic treatment.

The removable section 14 includes a polymeric body 16 that engages with the palatal structure of the dental model 12. The polymeric body 16 may be composed of various materials, including rigid acrylic polymers such as polymethylmethacrylate, soft polymers such as a polydimethylsiloxane, or thermoformed polymers such as polycarbonate. Preferably and as shown, polymeric body 16 has a custom-formed outer surface with a configuration that precisely matches and matingly fits at least a portion of the configuration of the lingual soft tissue 29 of dental model 12. As used herein, the lingual soft tissue 29 may include any of the mucosal surfaces in the oral cavity located in the lingual direction relative to the teeth, including for example the attached gingiva and palate of the upper arch and attached gingiva and adjacent tissue of the lower arch.

Optionally and as shown, the polymeric body 16 has facial edges that are spaced away in the lingual direction from the gingival margins of the teeth by gaps 15. By creating open space between the teeth and the polymeric body 16, the gaps 15 advantageously provide freedom to translate or tip teeth inward towards the lingual direction. On the other hand, if lingual tooth movement is not needed, the polymeric body may extend up to the gingival margins and lingually engage the undercuts or neck regions of some or all of the teeth. Engagement of the undercuts of teeth, particularly those that do not require correction, can be useful for securing removable section 14 against the soft tissues 29 when placed in the mouth and provide additional anchorage. In FIG. 1, the polymeric body 16 is horseshoe-shaped, but as an alternative may instead substantially cover the entire palatal region of dental model 12. If desired, polymeric body 16 may be formed from two or more separate sections that fit against different portions of the palate. If separate sections are used, they may be attached together using wire connectors or the like.

A plurality of wire members 18 are attached to polymeric body 16 and extend outwardly toward the teeth of dental model 12. The outer end of each wire member 18 is connected to a first coupling 30. Each of the wire members 18 corresponds to one of the upper central 20, lateral 22, cuspid 24, first bicuspid 26 and second bicuspid 28 teeth of the dental model 12. One or more of the wire members 18 shown in FIGS. 1 and 2 may be omitted if some of the teeth 20,22,24,26,28 are absent or do not require correction. One or more wire members 18 may also be omitted if some lingual tooth surfaces are inaccessible because of obstructions presented by neighboring teeth. The wire members 18 may have a cross-section that is rectangular, round, elliptical or any other shape. Since these wires are located on the lingual side of the teeth, however, it is preferable that wire members 18 have rounded surface contours for patient comfort during treatment.

As indicated in the exploded fragmentary view of FIG. 2, each first coupling 30 of removable section 14 connects with a second coupling 50 connected to a corresponding anchor 48. The paths of connection between the first couplings 30 and the second couplings 50 are shown by broken lines. Each anchor 48 is in turn connected to the respective lingual surface of a corresponding upper central 20, lateral 22, cuspid 24, first bicuspid 26 or second bicuspid 28 tooth on the dental model 12. The connection between the anchors 48 and respective teeth may be made by bonding, for example, using a suitable adhesive or cement. The anchors 48 need not be adhesively bonded. For example, the anchor 48 may be welded to an orthodontic band and the band subsequently secured to the respective tooth using a suitable band cement. In some embodiments, anchors 48 are bondable lingual buttons or other commercially available off-the-shelf bondable appliances. As a further alternative, anchors 48 may be formed entirely from a curable composite dental material, such as TRANSBOND brand light cure adhesive, and cured in vivo on the patient's teeth using techniques such as those described in U.S. Patent Application No. 2007/0031774.

In some embodiments, anchors 48 are accurately placed and bonded in precise, pre-selected positions of the lingual tooth surfaces of a patient. To this end, it can be advantageous to use indirect methods such as those described in issued U.S. Pat. No. 7,020,963 (Cleary, et al.) and U.S. Patent Publication Nos. 2006/0166160 (Cleary, et al.) and 2006/0177791 (Cinader, et al.).

The wire members 18 may be constructed from various materials displaying a wide range of material properties, such as stiffness and resiliency. The wire members 18 may also be individually configured based on the needs of the treating professional. For example, a given wire member 18 may be made from stainless steel when a high level of corrective force is desired, nickel titanium for a lower level of force, and beta titanium for an intermediate level of force. Some or all of the wire members 18 may be composed of other materials, including non-metallic materials such as polymers or filled composites. Furthermore, the length and thickness of each wire member 18 can be tailored to provide the desired stiffness.

In some embodiments, the wire members 18 are modular components that releasably connect to the removable section 14. For example, the wire members 18 may be inserted into an aperture sized to provide a friction-fit coupling, while also allowing individual wire members 18 to be removed from the polymeric body 16 when a sufficiently high pulling force is applied. Alternatively, a releasable latch or other mechanical coupling may be used. Preferably, the forces experienced by the wire member 18 during the normal course of treatment are well below the minimum force level required to displace or remove the wire member 18 from the polymeric body 16. By providing a means for wire members 18 to be removed from the polymeric body 16 and replaced with new wire members, it is possible to adjust or re-activate forces on the teeth as needed during treatment. The replacement wire member, for example, may be differently shaped, shorter, longer, stiffer or softer compared to the original wire member 18 to allow any number of different configurations of the appliance 10 depending on the progress of treatment. It is worth noting that the same polymeric body 16 need not be re-configured, since the polymeric body 16 fits against portions of the patient's oral structure that generally retain the same shape throughout treatment.

Optionally and as shown, the wire members 18 include flexible springs 36 that allow longitudinal movement (i.e. in a direction generally along the direction of extension of the wire members 18 away from the polymeric body 16) of the outer ends of the wire members 18 with respect to the polymeric body 16. The springs 36 furthermore increase the flexibility of the wire members 18. Preferably, the springs 36 are resilient and can deliver tensile or compressive forces in the longitudinal direction. Various types of springs 36 may be used, including Z-springs, coil springs, omega loops, pushrods, or any combinations thereof. By increasing flexibility of the wire members 18 and allowing longitudinal deflection, the springs 36 can facilitate connecting the wire members 18 to anchors 48 when the teeth are maloccluded. By operating in both tension and compression, the springs 36 also enable the appliance 10 to exert both intrusive and extrusive forces to the teeth. This is an important advantage over other removable appliances in the art, which usually have difficulty gripping the teeth to provide intrusive and extrusive tooth corrections. Based on the patient's treatment plan, the springs 36 may be provided on some or all of the wire members 18. In FIG. 1, the springs 36 are present in the wire members 18 connected to the centrals 20, but not present in the wire members 18 connected to the first bicuspids 26 or second bicuspids 28.

Optionally and as shown, clasps 38 are connected to the polymeric body 16 and secure the posterior areas of the removable section 14 to first molars 40 of the dental model 12. The clasps 38 are typically metal wire loops that extend over the occlusal surfaces of the mesial and distal embrasures of the first molars 40 and engage the facial surfaces of first molars 40 to secure removable section 14 against the dental model 12. While the clasps 38 depicted in FIGS. 1 and 2 are of the Adams clasp variety, other types of configurations are also possible, including arrowhead clasps, ball clasps, circumferential clasps and delta clasps. If desired, the clasps 38 may be further extended to engage one or both second molars 42. Engaging the second molars 42 with the clasps 38 can help facilitate seating of the removable section 14 in the mouth and provide an additional source of anchorage for applying corrective forces to the anterior teeth.

Figure 3:
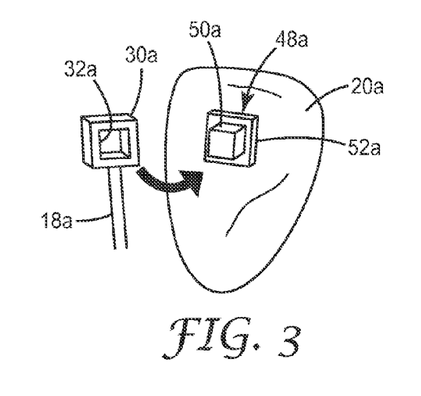
FIG. 3 is a fragmentary exploded view of one type of releasable coupling between the outer wire portion of the removable section and a respective anchor.

As the removable section 14 is moved in a generally gingival direction into abutting relationship with the lingual soft tissues 29 of the dental model 12, the outer end of each wire member 18 releasably connects with a respective anchor 48 connected to a respective tooth. FIGS. 3-6 show various geometric constructions which can be used to connect the outer end of a given wire member 18 with a given respective anchor 48. In each of these figures, the outer end of the wire member 18 is peeled away from the respective tooth surface to reveal the mating surfaces and the path to connection indicated by a curved block arrow. In FIG. 3, the outer end of wire member 18a is connected to a first coupling 30a, which further includes a cavity 32a with a rectangular cross-section. Optionally, the cavity 32a extends completely through the coupling 30a to form an aperture. Also shown in FIG. 3, an anchor 48a extends outwardly from a base 52a, which is in turn attached to the lingual surface of respective tooth 20a.

In some embodiments the base 52a has a tooth-facing surface contour that is customized to fit the lingual surfaces of tooth 20a. Having a customized base 52a can advantageously allow the anchor 48a to be configured with a lower profile for patient comfort. As a further advantage, a customizing the base 52a to the lingual surfaces of the tooth 20a could provide a self-positioning "lock and key" mechanism, where base 52a has contours that only allow anchor 48a to be mounted on the teeth 20a in a unique, well-defined location and orientation. Related methods used to form customized bondable lingual appliances are described in issued U.S. Pat. No. 6,776,614 (Wiechmann, et al.) and U.S. Patent Application Publication Nos. 2005/0158686 (Wiechmann, et al.), 2005/0003321 (Wiechmann, et al.), and 2005/0277084 (Cinader, et al.).

Located on the lingual side of anchor 48a is a second coupling 50a that protrudes outwardly from base 52a and has a generally rectangular cross-section. As the removable section 14 is moved in a generally gingival direction into an abutting relationship with the lingual soft tissue 29 of dental model 12, the second coupling 50a slides in the gingival direction across the lingual surface of the tooth 20a. Once the second coupling 50a slides into alignment with the first coupling 30a, the second coupling 50a labially descends into and securely engages with the rectangular cavity 32a of the first coupling 30a. As shown, the first coupling 30a and second coupling 50a have complementary mating surfaces that precisely register the outer end of the wire member 18a and respective anchor 48a with each other. Optionally, rectangular cavity 32a has a funneled entrance to facilitate aligning and engaging couplings 30a,50a with each other. Preferably, when the first coupling 30a and second coupling 50a are connected with each other, the location and orientation of the outer end of wire member 18a is precisely defined in three planes of space and three axes of rotation relative to anchor 48a.

Optionally and as shown, one or both of the couplings 30a,50a are magnetic couplings. For example, the first coupling 30a, the second coupling 50a, or both, may be at least partially constructed from a ferromagnetic material—that is, an object or material that generates a magnetic field in absence of an external magnetic field. Preferably, the magnetic portions of the couplings 30a,50a have polarities oriented such that a magnetic attractive force is created between opposing surfaces of the couplings 30a,50a. For example, the labial surface of the first coupling 30a may have a positive polarity, while the lingual surface of second coupling 50a may have a negative polarity. It is further preferred that the magnetic couplings 30a,50a are configured such that the first coupling 30a and second coupling 50a spontaneously and fully "snap" into proper connection when couplings 30a,50a are generally urged towards one another along a facial-lingual reference axis and reach a threshold proximity to each other. Preferably, one or both of the magnetic couplings 30a,50a retain their magnetic properties during the course of treatment.

The magnetic couplings 30a,50a have several advantages over non-magnetic, mechanical couplings. First, the magnetic fields produced by magnetic couplings 30a,50a operate even when there is no physical contact between the couplings 30a,50a. Even from a distance, these magnetic fields provide forces that attract the couplings 30a,50a with each other, and thereby facilitate seating the removable section 14 in a patient's mouth. Based on the tendency of magnets to commonly align with magnetic fields, the magnetic couplings 30a,50a are also self-aligning. Provided there is a sufficient attractive force between magnetic couplings 30a,50a, it is possible for a patient or treating professional to conveniently connect couplings 30a,50a with each other simply by urging them towards each other from any angle or direction (including mesial, distal, occlusal, and gingival). Particularly in cases where there are a plurality of wire members and respective anchors, magnetic engagement provides a substantial ease-of-use benefit and time savings over purely mechanical engagement.

As a further advantage, the magnetic attraction between couplings 30a,50a provides force to retain the protruding portion of coupling 50a in the cavity of coupling 30a. In this manner, couplings 30a,50a actively resist spontaneous or accidental disengagement from one another. This is an important advantage when the appliance 10 is being worn by a patient during orthodontic treatment, since couplings 30a,50a should be sufficiently robust to remain connected during the normal course of speech, chewing action (if appliance 10 is worn while eating), tongue thrusts, and so forth.

As another advantage, the magnetic retaining force between couplings 30a,50a allows wire members 18 to impart both "pushing" (facial) and "pulling" (lingual) forces to the teeth during treatment. As a result, appliance 10 displays a major advantage in versatility and control over conventional wire-embedded appliances, which generally only apply "pushing" forces on the teeth. In order for these conventional appliances to apply forces in the lingual direction, wires are typically guided across the labial sides of the teeth, which is not preferred for aesthetic reasons.

As yet another advantage, magnetic couplings 30a,50a do not require mechanical retention with each other and can therefore be configured with mating surfaces that are free of undercuts. This is a substantial benefit to the patient, since undercut surfaces tend to trap food and plaque. Elimination of these undercuts is especially beneficial with lingual appliances, which can be difficult to clean. For the same reasons, it is preferable that the lingual surfaces of anchors 48 are configured to be free of undercuts.

Figure 4:
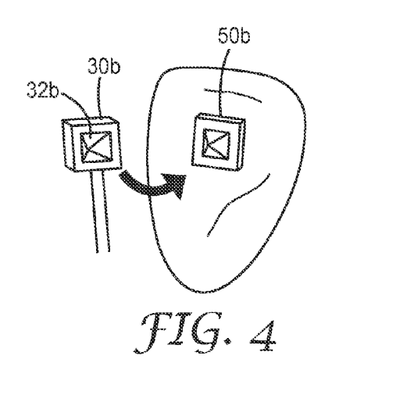
FIG. 4 is a fragmentary exploded view of another type of releasable coupling between the outer wire portion of the removable section and a respective anchor.
Figure 5:
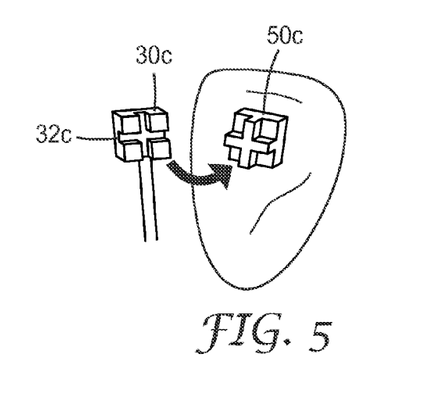
FIG. 5 is a fragmentary exploded view of still another type of releasable coupling between the outer wire portion of the removable section and a respective anchor.

Other advantageous geometric constructions are shown in FIGS. 4 and 5. For example, FIG. 4 shows an alternative embodiment where first coupling 30b and second coupling 50b are configured with pyramidal mating surfaces. In this embodiment, the first coupling 30b has a pyramidal cavity 32b that releasably connects with a pyramidal protrusion on the second coupling 50b. The tapered walls of the pyramidal cavity 32b are advantageous because they are self-guiding and allow for minor misalignment when engaging couplings 30b,50b. By facilitating the pair-wise connection of couplings 30b,50b across the entire arch, the tapered walls of the pyramidal cavity 32b allow the removable section 14 to be connected and disconnected from the anchors 48 quickly and easily.

Figure 6:
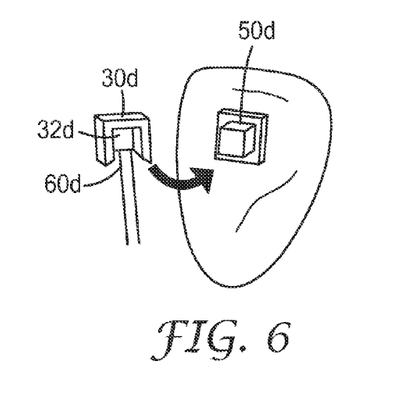
FIG. 6 is a fragmentary exploded view of yet still another type of releasable coupling between the outer wire portion of the removable section and a respective anchor.

FIG. 5 shows an alternative embodiment in which a first coupling 30c with a cross-shaped cavity 32c connects with a second coupling 50c with a matching, generally cross-shaped protrusion. FIG. 6 shows still another alternative embodiment that includes a first coupling 30d with an open-ended rectangular cavity 32d and respective second coupling 50d. The first coupling 30d differs from those above in that the cavity 32d has no gingival wall, allowing for lateral connection by sliding coupling 30d towards coupling 50d from the occlusal direction. This is advantageous, from an ease of use perspective, since the outer ends of the wire members 18 generally approach the anchor 48 from the occlusal direction during patient installation. Optionally and as shown, the coupling 30d includes a funneled occlusal entry 60 to facilitate insertion of the protrusion in coupling 50d into the cavity of coupling 30d. The above embodiments are shown for exemplary purposes only, and other mating surface geometries are possible.

Mechanical couplings such as rails, slots, dovetails, undercuts, or other interlocking structures can also be used to releasably connect couplings 30,50 to each other. In some embodiments, one or both couplings 30,50 includes a clip, latch, or other flexible portion to provide mechanical connection. For example, the first coupling 30 could use a flexible aperture or cavity that resiliently enlarges in order to encircle and engage the second coupling 50, and then subsequently relaxes back to its original shape to securely connect the couplings 30,50 to each other. Alternatively, the first coupling 30 could include a generally C-shaped clip that resiliently deflects open to receive the second coupling 50 as the removable section 14 is moved in a generally gingival direction into abutting relationship with the lingual soft tissue 29 of dental model 12. The first coupling 30 can then relax back to its original position to secure couplings 30,50 with each other. Examples of releasable couplings are described in issued U.S. Pat. No. 6,302,688 (Jordan, et al.), U.S. Pat. No. 6,582,226 (Jordan, et al.), U.S. Pat. No. 7,014,460 (Lai, et al.), U.S. Pat. No. 7,252,505 (Lai) and pending U.S. Patent Application Publication No. 2005/0277084 (Cinader et al.). Any of the above mechanical couplings can be used in combination with magnetic couplings if desired.

The forces required to connect and disconnect couplings 30,50 from each other should be sufficiently low to allow easy insertion and removal of the removable section 14 by the patient. It is also preferred, however, that these forces are sufficiently high that removable section 14 securely connects to the patient's dental structure and does not unintentionally detach from any of the anchors 48 during treatment. That is, couplings 30,50 should remain connected even when subjected to normal corrective forces and other forces encountered during treatment. In preferred embodiments, couplings 30,50 are configured to yield an engagement force that is as low as possible. The use of magnetic couplings is particularly advantageous in that the couplings 30,50 can be made essentially "self-engaging" and require no additional force from the user beyond that needed to bring couplings 30,50 into proximity with each other. In preferred embodiments, the disengagement forces are neither too high such that disengagement causes patient discomfort, nor too low such that spontaneous disengagement occurs during treatment. The optimal values for engagement and disengagement forces may vary considerably from tooth to tooth and depend in part on the configuration of the wire members 18.

Advantageously, the appliance 10 is capable of producing various types of tooth movement. The freedom to configure the wire members 18 and the precise manner in which the removable section 14 connects to the anchors 48 together allow appliance 10 to move teeth in ways that are very difficult using conventional aligners and wire-embedded appliances. Because each individual wire member 18 can be manipulated into a nearly limitless number of configurations, the appliance 10 has the potential to produce any combination of in-out and mesial-distal tooth movements, as well as tipping and rotational tooth movements. As mentioned earlier, even intrusive and extrusive tooth movements parallel to the longitudinal axis of the wire member 18 are made possible by incorporating one or more flexible springs 36 into the wire member 18.

Figure 7:
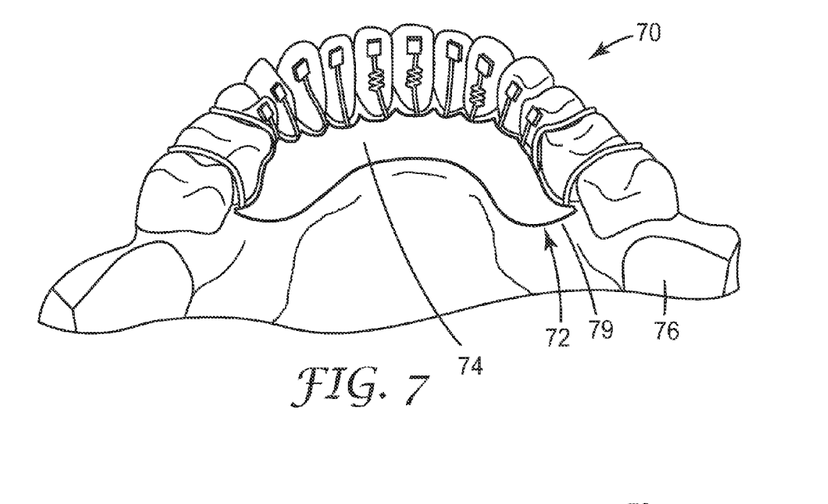
FIG. 7 is a perspective view of a lower arch removable appliance according to one embodiment of the invention attached to a physical dental model.
Figure 8:
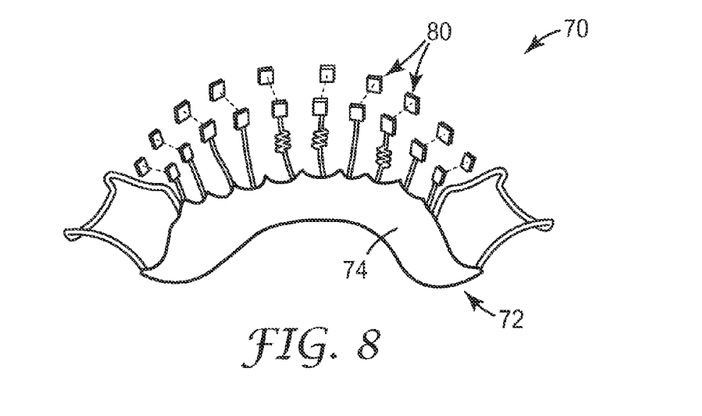
FIG. 8 is an exploded, perspective view of a removable section of the appliance of FIG. 7 detached from the physical dental model.

Referring now to the embodiment depicted in FIGS. 7 and 8, a lower appliance 70 according to another aspect of the invention is configured for orthodontic correction of the lower arch. Lower arch appliance 70 is structurally similar in many respects to upper arch appliance 10 in that it includes a removable section 72 along with anchors 80, which are in turn connected to the teeth of dental model 76. Appliance 70 is shown connected to the lingual tooth surfaces of dental model 76 in FIG. 7 and furthermore shown in exploded view, with dental model 76 removed, in FIG. 8. The removable section 72 has a generally horseshoe-shaped polymeric body 74 adapted to fit against the lingual soft tissue 79 of the lower arch, while preferably avoiding contact with the teeth of the lower arch.

In some embodiments, the polymeric body 74 has an outer surface with a configuration that generally matches the configuration of the attached gingiva between the tongue and the undercuts of the lower incisors. Here, the attached gingiva is delineated from the unattached gingiva below it by the mucogingival line. Preferably, the polymeric body 74 does not extend onto the unattached gingiva, since the movement of these soft tissues during speech and swallowing may cause discomfort, abrasions and/or ulceration in the patient. The attached gingiva is fixed and thereby resistant to this phenomenon. Other aspects of appliance 70 are analogous to those of appliance 10 and shall not be repeated here.

Other embodiments are also possible. For example, the upper and lower arch appliances 10,70 can be used in combination with temporary anchorage devices ("TADs") that are implanted in the palate or jawbone. This may be accomplished by coupling the polymeric body 16,74 to one or more TADs, or alternatively by configuring one or more wire members 18 to releasably connect with respective TADs. By engaging with implanted devices such as TADs, it is possible to further supplement the anchorage available to the treating professional and reduce the need for extraoral anchorage, such as that provided by headgear. Examples of orthodontic applications for TADs are provided in issued U.S. Pat. No. 6,716,030 (Bulard et al.) and U.S. Pat. No. 6,726,475 (Lin), published U.S. Patent Application Nos. 2007/264607 (Olavarria), and PCT application No. 2007/128969 (Cousley).

In still other embodiments, the anchor 48,80 itself may be elongated and extend across the lingual surfaces of two or more adjacent teeth along the dental arch. The anchor 48,80 may furthermore be adhesively bonded or otherwise connected to two or more adjacent teeth along the dental arch. By connecting two or more teeth to each other, the anchor 48,80 advantageously fixes the positions of the connected teeth relative to each other, while still allowing the teeth to be moved together as a unit. Alternatively, anchors 48,80 located on two different teeth may be joined together with a rigid structure such as a lingual wire segment or lingual strap. If one or more teeth are located along the arch between the anchors 48,80, the wire segment or strap can advantageously be used to constrain the lingual movement of these teeth.

There need not be a one-to-one correlation between anchors 48,80 and wire members 18. It is possible for two or more wire members 18 to be connected to a single anchor 48,80 at two or more respective locations. Alternatively, it is possible for a single wire member 18 to be connected to an anchor 48,80 that is, in turn, joined with one or more other anchors 48,80 as described in the preceding paragraph. These possibilities provide a treating professional greater versatility in configuring appliance 10,70 to retain, or direct corrective forces to, the teeth. As an added advantage, these configurations can reduce the total number of wire members 18 and/or anchors 48,80 in the mouth of the patient, and thereby enhance patient comfort during treatment.

Methods of Making

Figure 9:
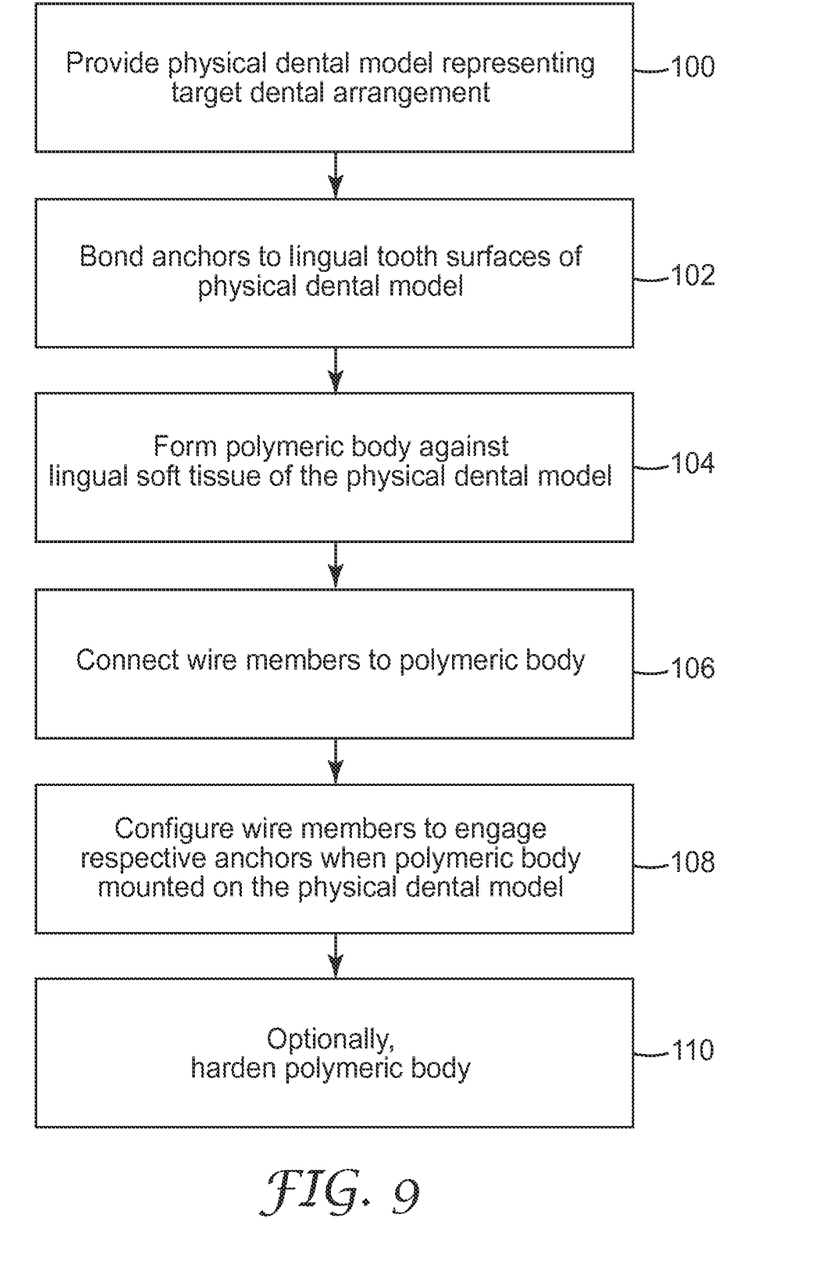
FIG. 9 is a flowchart showing exemplary steps in fabricating the appliance of FIG. 1 or 7.

An exemplary process followed by a treating professional or laboratory technician to fabricate the appliance 10,70 is described by the flowchart in FIG. 9. An initial step is to provide a physical dental model 12,76 used to form the appliance 10,70, as represented by block 100 on the flowchart. The configuration of the dental model 12,76 preferably represents a target dental arrangement as perceived by the treating professional. As defined herein, the "target dental arrangement" may be a patient's current dental arrangement, a desired final dental arrangement, or a predicted intermediate dental arrangement, depending on the application contemplated by the treating professional.

If the target dental arrangement is defined as the patient's current dental arrangement, then the dental model 12,76 can be provided, for example, from an epoxy resin or stone casting prepared from an alginate impression of a patient's dentition. If target dental arrangement is defined as an intermediate or final dental arrangement, then the above casting may be sectioned into individual model tooth elements, the tooth elements rearranged to form the desired dental arrangement, and the tooth elements waxed back together to provide the dental model 12,76. Alternatively, the dental model 12,76 may also be a reconfigurable dental model, thereby allowing individual teeth to be rearranged without sectioning. Examples of reconfigurable dental models are described, for example, in issued U.S. Pat. No. 6,227,851 (Chishti et al.) and U.S. Pat. No. 6,394,801 (Chishti et al.).

Once provided, the dental model 12,76 can be used as a template to make and configure the appliance 10,70. This process continues with block 102, in which the anchors 48,80 are connected to the respective lingual tooth surfaces of the dental model 12,76. The polymeric body 16 is then formed against the replica lingual soft tissue 29,79 of the dental model 12,76 using a suitable thermoplastic or curable acrylic, as provided in block 104. Examples of such materials include, but are not limited to, TRIAD TRANSHEET brand light curable acrylic from Dentsply International (York, Pa.) and BIOCRYL brand cold curable acrylic resin from Great Lakes Orthodontics (Tonawanda, N.Y.). Once the shape and outer surface of the polymeric body 16 have been properly formed, the wire members 18 are inserted into the polymeric body 16 as indicated in block 106.

As shown in block 108, each wire member 18 is then configured such that it releasably connects with the anchors 48,80 as the removable section 14,72 is moved into abutting relationship with the replica lingual soft tissue 29,79 of dental model 12,76. Optionally and as indicated in block 110, the polymeric body 16,74 is hardened in its final shape by means of an appropriate curing (i.e. cross-linking) reaction. The hardening step of block 110 may also take place before the configuration of the wire members 18, if desired. After the removable section 14,72 has been fully configured, it is disconnected from the anchors 48,80 and set aside.

To use the appliance 10,70, the anchors 48,80 need to be transferred from the dental model 12,76 to the patient's teeth. To preserve the precise locations of the anchors 48,80 relative to the respective teeth, this step is preferably carried out using an indirect bonding tray or other transfer apparatus. If the anchors 48,80 are customized to the lingual surfaces of the patient's teeth and thereby self-positioning, direct bonding may be an viable alternative. The removable section 14,72 can then be placed in the patient's mouth and connected to the anchors 48,80 to commence orthodontic treatment.

The foregoing passages describe exemplary methods of making and using the appliance 10,70, but many other embodiments are possible. For example, one or more of the steps in blocks 100, 102, 104, 106, 108, and 110 may be performed with the assistance of digital methods. By performing operations in a virtual world, it is also possible for one or more of these steps to be consolidated or even eliminated. Various digital methods, as will be described further below, can potentially improve the precision of appliance design as well as facilitate aspects of the fabrication process that are traditionally done by hand.

One such method is digital scanning. A virtual dental model representing the patient's dental structure may be captured using a digital intraoral scan or by digitally scanning an impression or dental model. From there, it is possible for a treating professional to manipulate the virtual dental model on a computer, for example, in order to arrive at the target dental arrangement referred to in block 100. Further details on software and processes that may be used to derive the target dental arrangement are disclosed, for example, in U.S. Pat. No. 6,739,870 (Lai, et al.), U.S. Patent Application Publication Nos. 2005/0170309 (Raby, et al.), 2006/0073435, 2006/0073436 (Raby, et al.), and 2006/0105286 (Raby, et al.), and U.S. Patent Application Publication No. US2008/0233531 (Raby et al.).

Another digital method that can facilitate preparation of the dental model 12,76 is rapid prototyping. After a virtual dental model has been created using any of the above methods, rapid prototyping techniques allow the dental model 12,76 to be directly fabricated from this virtual dental model. Advantageously, there is no need to take an alginate impression or cast a stone model. Examples of rapid prototyping techniques include, but are not limited to, three-dimensional (3D) printing, selective area laser deposition or selective laser sintering (SLS), electrophoretic deposition, robocasting, fused deposition modeling (FDM), laminated object manufacturing (LOM), stereolithography (SLA) and photostereolithography. These and other methods of forming a positive dental model from scanned digital data are disclosed in pending provisional U.S. Patent Application Ser. No. 60/975,687 (Puffler, et al.). As can be appreciated, the step of providing the dental model 12,76 in block 100 can be assisted, to a large extent, by using digital scanning and rapid prototyping methods.

In other embodiments, the anchors 48,80 are connected to the patient's teeth prior to taking an impression or intraoral scan. Since the anchors 48,80 are directly bonded to the patient's teeth, this simplifies the process by eliminating the need to bond the anchors 48,80 to the physical dental model 12,76 in block 102, as well as the need to transfer the anchors 48,80 to the patient's teeth. As before, the manipulation of the dental model 12,76 from the maloccluded dental arrangement to the target dental arrangement may be carried out on a computer. There are other potential benefits. For example, if the anchors 48,80 and the patient's teeth are captured together in an intraoral scan, it is possible to digitally configure the wire members 18 of the removable section 14,72 using a wire bending apparatus or robot based on the relative locations of the anchors 48,80 and the patient's teeth.

Rapid prototyping may even eliminate the need to provide a physical dental model 12,76 for fabricating the appliance 10,70. While it has been shown that rapid prototyping can be used to fabricate dental model 12,76, it is also conceivable that rapid prototyping could be used to directly fabricate at least a portion of the appliance 10,70. The forming of the polymeric body 16,74 in blocks 104 and 110, the configuration of wire members 18 in blocks 106 and 108, and/or the configuration of the anchors 48,80 and the couplings 30,50 could potentially be carried out with the assistance of rapid prototyping techniques. Direct fabrication can provide potential cost and time savings by eliminating intermediate steps in the fabrication of the appliance 10,70.

In the event that the appliance 10,70 is directly fabricated from a virtual dental model, a physical dental model 12,76 may still be useful to verify the appliance 10,70 for quality control purposes. This may be carried out by seating the removable section 14,72 against a physical dental model 12,76 and observing that the outer ends of each wire member 18 releasably connect to a respective anchor 48,80 as the removable section 14,72 is seated against the physical dental model 12,76. Assuming that the appliance 10,70 is properly configured and the dental model 12,76 represents the target dental arrangement, each of the wire members 18 should be relaxed when the removable section 14,72 is seated. The above procedure can also be used to verify the appliance 10,70 on a dental model representing a maloccluded (or non-desired) dental arrangement to ensure that the outer ends of each wire member can properly connect to its respective anchor 48,80. In this case the appliance 10,70 is active, so at least one wire member 18 should be acting in force-transmitting engagement upon seating the removable section 14,72.

As an added benefit, it is also possible for the removable section 14,72 of the appliance 10,70 to be re-configured during the course of treatment. Re-configuring the removable section 14,72 can be an efficient and cost-effective alternative to fabricating a series of removable sections 14,72. For example, the removable section 14,72 may be re-configured to guide teeth through two or more dental arrangements during the course of treatment by making manual adjustments (e.g. bends) to one or more of the wire members 18. This can also be used advantageously to re-activate the appliance 10,70. For example, if the patient's teeth have moved to an extent that the current appliance 10,70 is no longer exerting sufficient force to effect tooth movement, the treating professional has the freedom to restore the corrective forces applied by the appliance 10,70 by making appropriate adjustments to the wire members 18. If the wire members 18 are modular, then this adjustment can take place through the replacement of one or more individual wire members 18 in the removable section 14,72. Optionally, the locations of the anchors 48,80 are captured beforehand using an intraoral scan or other scanning technique, and this information used to configure the replacement wires automatically using a wire bending apparatus or robot.

Applications

Various applications for the appliance 10,70 are contemplated. In one application, the appliance 10,70 functions as a retainer that maintains the patient's teeth in their current positions. For this application, the dental model 12,76 used to fabricate appliance 10,70 is an exact replica of the patient's current dental structure. Since the dental model 12,76 has the same configuration as the patient's dental structure, appliance 10,70 would be applying essentially zero force to the teeth when placed in the mouth. In the event that one or more of the teeth relapse, or change location or orientation, then the appliance 10,70 urges the wayward teeth back to their original positions.

In a second application, appliance 10,70 is configured to actively move teeth from current maloccluded positions to final, desired positions. More specifically, as the removable section 14,72 of the appliance 10,70 is moved into abutting relationship with the patient's soft lingual tissue and connects with the anchors 48,80, at least one of the wire members 18 resiliently deflects. The inherent memory of the resilient, deflected wire members 18 will then provide corrective forces on the teeth as the wire members 18 relax back to their normal configuration. In this application, the dental model 12,76 used to fabricate the appliance 10,70 therefore represents the final dental arrangement envisioned by the treating professional.

In a third application, appliance 10,70 is configured to move teeth to an intermediate, non-final dental arrangement. This situation may be encountered when the severity or complexity of the malocclusion is such that a single appliance is insufficient to reposition teeth from initial to final positions. In these cases, treatment may be conducted in multiple stages where a series of two or more removable sections 14,72 are sequentially used with a single set of anchors 48,80 to incrementally and progressively move teeth from an initial maloccluded dental arrangement to a final corrected dental arrangement. Here, the dental model 12,76 used to fabricate the appliance 10,70 represents an intermediate dental arrangement that may be observed during the course of treatment.

In an exemplary embodiment of the third application, a first removable section 14,72 is connected to the anchors 48,80 to re-position a patient's maloccluded teeth to an intermediate dental arrangement. The first removable section 14,72 is then removed from the oral cavity. Next, a second removable section that has a configuration when relaxed that is different from the configuration of the first removable appliance section when relaxed, can be used in a similar fashion to re-position the patient's teeth from the intermediate dental arrangement to a final dental arrangement. If desired, the above process can be extended to two or more intermediate dental arrangements.

As before, dental models 12,76 representing intermediate or final dental arrangements can be fabricated by manually forming, sectioning, and re-assembling a physical dental casting. Digital methods may also be used. For example, a final dental arrangement can be determined using a computer algorithm or input from treating professional, and one or more intermediate dental arrangements derived by subdividing the treatment into a series of discrete steps. Once each intermediate or final dental arrangement has been derived in such fashion, respective dental models 12,76 may be directly fabricated using rapid prototyping methods. Each respective intermediate or final removable section 14,72 may finally be fabricated from the dental models 12,76 using any of the methods already described.

The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

The invention claimed is:

1. An orthodontic appliance comprising:
a removable section including a polymeric body and one or more elongate members extending outwardly from the body, the polymeric body including a posterior area and an anterior area, wherein each elongate member of the one or more elongate members includes an outer end portion including a first coupling, wherein the body includes an outer surface with a configuration that generally matches the configuration of a patient's lingual soft tissue, and wherein at least one elongate member extends from the anterior area of the body to the first coupling in a generally mesial direction towards the position of the patient's central, lateral, or cuspid teeth; and
one or more anchors, each anchor having a base for connecting the anchor to the lingual surface of a tooth and a second coupling extending outward from the base, at least one anchor of the one or more anchors configured to connect to the lingual surface of the patient's central, lateral, or cuspid teeth, wherein the second coupling of each anchor is releasably received in a first coupling of a respective elongate member when each anchor is connected to a respective tooth of a dental patient.

2. The appliance of claim 1, wherein the outer surface with a configuration that generally matches the configuration of a patient's lingual soft tissue generally matches the patient's palate.

3. The appliance of claim 1, wherein each elongate member comprises a wire member.

4. The appliance of claim 1, wherein the first and second couplings include magnetic couplings.

5. The appliance of claim 1, wherein the first and second couplings include mating surfaces that register the outer end portion of each wire member and the respective anchor to each other.

6. The appliance of claim 5, wherein the second coupling has an exterior shape, and wherein the first coupling comprises a cavity having a geometry that approximates the exterior shape of the second coupling.

7. The appliance of claim 6, wherein the second coupling includes a protrusion having a tetrahedral shape.

8. The appliance of claim 6, wherein the second coupling includes a protrusion having a pyramidal shape.

9. The appliance of claim 1, wherein the first coupling includes an aperture that encircles the second coupling.

10. The appliance of claim 9, wherein the aperture is flexible and resiliently enlarges to accept the second coupling.

11. The appliance of claim 1, wherein at least one of the first couplings includes a funneled recess to facilitate engagement of the second coupling.

12. The appliance of claim 1, wherein the first coupling member surrounds the second coupling member when connected.

13. The appliance of claim 1, wherein the first coupling comprises a generally C-shaped clip.

14. The appliance of claim 1, wherein the at least one wire member extending from the anterior area comprises a flexible spring that allows movement of the outer ends of the wire member in a direction generally along the mesial direction of extension of the wire members away from the polymeric body.

15. The appliance of claim 1, wherein the base of at least one anchor has a tooth-facing surface contour that is customized to fit the lingual surfaces of the tooth.

16. An orthodontic appliance comprising:
a removable section including a polymeric body and one or more elongate members extending outwardly from the body, the polymeric body including a posterior area and an anterior area, wherein each elongate member of the one or more elongate members includes an outer end portion including a first coupling, wherein the body includes an outer surface with a configuration that generally matches the configuration of a patient's lingual soft tissue, and wherein at least one elongate member extends from the anterior area of the body to the first coupling in a generally mesial direction towards the position of the patient's central, lateral, or cuspid teeth; and
one or more anchors, each anchor having a base for connecting the anchor to the lingual surface of a tooth and a second coupling extending outward from the base and defining a recessed area, at least one anchor of the one or more anchors configured to connect to the lingual surface of the patient's central, lateral, or cuspid teeth, and wherein the first coupling of each elongate member is releasably received in the second coupling of a respective anchor when each anchor is connected to a respective tooth of a dental patient.

17. The appliance of claim 16, wherein the first coupling has an exterior shape, and wherein the second coupling comprises a cavity having a geometry that approximates the exterior shape of the first coupling.

18. The appliance of claim 16, wherein the second coupling includes an aperture that encircles the first coupling.

19. The appliance of claim 16, wherein the second coupling includes a cavity that releasably engages a portion of the first coupling.

20. A method of orthodontic treatment comprising:
attaching a plurality of anchors to a lingual surface of one of a patient's central, lateral, and cuspid teeth, the anchors comprising base for bonding to a tooth surface and a first coupling projecting outwardly from the base;
providing a removable section including a polymeric body and at least one elongate member extending outwardly from an anterior area of the body, wherein each elongate member includes an outer end portion having a second coupling and the body includes an outer surface with a configuration that generally matches the configuration of a patient's lingual soft tissue;
and proximate the central, lateral, and cuspid teeth;
releasably connecting the second coupling of each elongate member to a respective anchor; and
placing the polymeric body adjacent the patient's lingual soft tissue.

21. A method of orthodontic treatment of claim 20, wherein the removable appliance section is a first removable appliance section, and further including:
removing the first appliance section from the oral cavity;
moving a second removable appliance section in the patient's oral cavity, wherein the second removable appliance section includes a polymeric body and at least one elongate member extending outwardly from the polymeric body of the second removable appliance section, and wherein the second removable appliance section has a configuration when relaxed that is different from the configuration of the first removable appliance section when relaxed; and
connecting a second coupling of each elongate member of the second removable appliance section to a respective anchor.

* * * * *